United States Patent [19]

Krüger et al.

[11] Patent Number: 4,900,834
[45] Date of Patent: Feb. 13, 1990

[54] SUBSTITUTED α,ω-AMINOALCOHOL DERIVATIVES

[75] Inventors: Bernd-Wieland Krüger, Wuppertal; Klaus Sasse, Bergisch-Gladbach; Franz-Peter Hoever, Cologne; Günther Nentwig, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 183,941

[22] Filed: Apr. 20, 1988

[30] Foreign Application Priority Data

Apr. 28, 1987 [DE] Fed. Rep. of Germany ....... 3714058
Jan. 16, 1988 [DE] Fed. Rep. of Germany ....... 3801082

[51] Int. Cl.$^4$ .......................................... C07D 211/22
[52] U.S. Cl. ................................... 546/245; 540/608; 548/531; 560/160; 562/555
[58] Field of Search ................. 546/245; 548/531; 540/608

[56] References Cited

U.S. PATENT DOCUMENTS 3,442,889 5/1969 D'Amico .............................. 540/608
4,555,515 11/1985 Wong ................................... 514/357

FOREIGN PATENT DOCUMENTS 0144825 6/1985 European Pat. Off. .
0169169 1/1986 European Pat. Off. .
1150973 2/1964 Fed. Rep. of Germany .

OTHER PUBLICATIONS

*Chemical Abstracts*, 103:141568y (1985) [Levendecker, F., et al., Nouv. J. Chem. 1985, 9(1), 7–12].
Coward, J., et al., *J. Org. Chem.*, 38(14), 2546–2548 (1973).
K. H. Buchel, Insekten–Repellants, in R. Wegler, *Chemie der Pflanzenschutz und Schadlingsbekampfungsmittel*, vol. 1, Springer Verlag, Berlin, 1970, pp. 487–497.
R. K. Kochhar, et al., *Indian J. Med. Res.* 62(1) pp. 125–133 (1984).

A. Dasgupta et al., *Indian J. Med. Res.* 61(1), pp. 1–7 (1973).
Patent Abstracts of Japan, vol. 9, No. 254 (C–308) [1977], 11th Oct. 1985 [JP-A-60 109 555 (Nihon Iyakuhin Kogyo K.K.) 15–06–1985].
*Chemical Abstracts*, 104; 5644 p. (1986) [JP-A-60 109 555, 6/15/85].

*Primary Examiner*—Richard A. Schwartz
*Attorney, Agent, or Firm*—Sprung, Horn, Kramer & Woods

[57] ABSTRACT

It has been found that the substituted α,ω-aminoalcohol derivatives, some of which are known, of the formula I

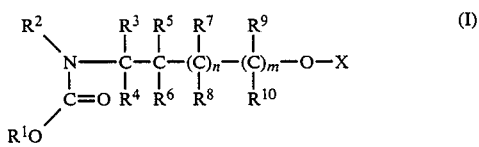

in which
X represents hydrogen, $COR^{11}$, $COOR^{12}$ or $R^{13}$,
$R^1$ represents optionally substituted alkyl, alkenyl or alkinyl radicals
$R^2$, $R^{11}$, $R^{12}$ and $R^{13}$ are identical or different and represent optionally substituted alkyl or alkenyl radicals,
$R^3$ to $R^{10}$ are identical or different and represent hydrogen, or represent optionally substituted alkyl radicals,
and wherein
$R^2$ and $R^3$ or $R^3$ and $R^7$ or $R^3$ and $R^5$ or $R^5$ and $R^7$, together with the atoms to which they are bonded, can also form an optionally substituted monocyclic ring, and
n and m are identical or different and denote 0 or 1,
with the proviso that X does not represent hydrogen or $R^{13}$ if n and m represent 0, have a powerful insect- and mite-repelling action (repellent action).

4 Claims, No Drawings

SUBSTITUTED α,ω-AMINOALCOHOL DERIVATIVES

The present invention relates to the use of substituted α,ω-aminoalcohol derivatives, some of which are known, as agents for repelling insects and mites. The present invention furthermore provides new substituted α,ω-aminoalcohol derivatives.

Agents which repel insects and mites (repellents) have the task of keeping harmful or troublesome arthropods from contact with and from stinging and sucking or biting surfaces which attract them, for example the skin of humans and animals, if these have first been treated with such agents.

Numerous active compounds have already been proposed as repellents. (Compare, for example, K. H. Buchel in Chemie der Pflanzenschutz- und Schadlingsbekampfungsmittel (Chemistry of Plant Protection and Pest Control Agents); publisher: R. Wegler, Volume 1, Springer Verlag Berlin, Heidelberg, New York, 1970 page 487 et seq.).

Compounds which are known in particular and have been used for a relatively long time are N,N-diethyl-3-methyl-benzamide (DEET), dimethyl phthalate and 2-ethyl-hexane-1,3-diol, of which above all DEET has achieved considerable importance in practice (see, for example, R. K. Kocher, R. S. Dixit, C. I. Somaya; Indian J. Med. Res. 62, 1 (1974)):

A considerable disadvantage of the known repellents is their in part relatively short (lasting only a few hours) persistent continuous action.

Some of the compounds defined by the following formula (I) are known.

In this context, see German Auslegeschrift (German Published Specification) No. 1,288,507, column 2, 1st formula where R denotes methyl. This is an intermediate in the preparation of ethyl N-(3-carbamoyloxyalkyl)-carbamate, which is used as a sedating medicament. In this context see also Published European Patent Application EP 0,144,825, A1, compound No. 37 on page 43 of the abovementioned publication, which is used as an intermediate for the preparation of antibiotic compounds.

However, an insect- and mite-repelling action of these compounds has not yet been disclosed.

It has now been found that the substituted α,ω-aminoalcohol derivatives, some of which are known, of the formula I

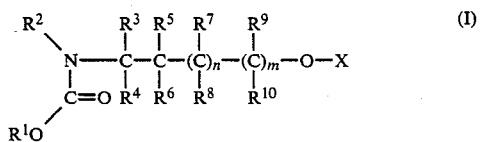

in which
X represents hydrogen, COR$^{11}$, COOR$^{12}$ or R$^{13}$,
R$^1$ represents optionally substituted alkyl, alkenyl or alkinyl radicals
R$^2$, R$^{11}$, R$^{12}$ and R$^{13}$ are identical or different and represent optionally substituted alkyl or alkenyl radicals,
R$^3$ to R$^{10}$ are identical or different and represent hydrogen, or represent optionally substituted alkyl radicals, and wherein
R$^2$ and R$^3$ or R$^3$ and R$^7$ or R$^3$ and R$^5$ or R$^5$ and R$^7$, together with the atoms to which they are bonded, can also form an optionally substituted monocyclic ring, and
n and m are identical or different and denote 0 or 1, with the proviso that X does not represent hydrogen or R$^{13}$ if n and m represent 0,
have a powerful insect- and mite-repelling action (repellent action).

The repellent action is considerably better than that of repellents known from the prior art. The active compounds according to the invention thus represent a valuable enrichment of the art.

The present invention thus relates to the use of substituted α,ω-aminoalcohol derivatives of the general formula I for repelling insects and mites.

The invention furthermore relates to agents for repelling insects and mites, characterized in that they contain at least one substituted α,ω-aminoalcohol derivative of the general formula I.

The agents according to the invention, which contain at least one derivative of the formula I, can also contain other insect repellents. Virtually all the customary repellents can be used here (compare, for example, K. H. Buchel in Chemie der Pflanzenschutz- und Schadlingsbekampfungsmittel (Chemistry of Plant Protection Agents and Pest Control Agents); publisher: R. Wegler, Volume 1, Springer Verlag Berlin, Heidelberg, New York, 1970, page 487 et seq.).

In the case of repellent combinations, the substituted α,ω-aminoalcohols of the general formula I are preferably used together with repellent carboxamides, 1,3-alkanediols and carboxylic acid esters. Compounds which may be mentioned specifically are: 3-methyl-benzoic acid diethylamide (DEET), 2-ethyl-hexane-1,3-diol (Rutgers 612) and dimethyl phthalate.

The substituted α,ω-aminoalcohol derivatives which can be used according to the invention are characterized by the general formula (I).

The radicals given in formula (I) preferably have the following meaning:

The alkyl group in the radicals R$^1$ to R$^{13}$ is straight-chain or branched and contains 1 to 12, preferably 1 to 8 and in particular 1 to 6, carbon atoms. Examples which may be mentioned are methyl, ethyl, n- and i-propyl, n-, i- and t-butyl, n-pentyl and n-hexyl.

Optionally substituted alkenyl is represented by straight-chain or branched alkenyl with preferably 2 to 10, in particular 2 to 7, carbon atoms. Examples which may be mentioned are optionally substituted 2-propenyl, 2-butenyl and 3-butenyl.

The radicals R$^2$ and R$^3$ or R$^3$ and R$^7$ or R$^3$ and R$^5$ or R$^5$ and R$^7$, together with the atoms to which they are bonded, can form 5 to 7-membered saturated rings which can be substituted by 1 or 2, preferably one, alkyl group, in particular methyl and ethyl.

The optionally substituted radicals R$^1$ to R$^{13}$ can carry one or more, preferably 1 to 3 and in particular 1 to 2, identical or different substituents. Substituents which may be mentioned are: alkyl with preferably 1 to 10, in particular 1 to 6, carbon atoms, such as methyl, ethyl, n- and i-propyl, n-, i- and t-butyl, cycloalkyl with preferably 3 to 7 carbon atoms such as cyclopropyl and cyclohexyl. Other possible substituents for R$^1$ to R$^{13}$ are, for example, C$_1$–C$_4$-alkoxy, halogen and CN.

Preferably, in the compounds of the general formula (I), one of the indices n and m represents 0 and the other represents 0 or 1, with the proviso that X does not represent hydrogen or R$^{13}$ if n and m represent 0.

Compounds of the general formula (I) which are preferably used as repellents are those
in which
X represents hydrogen, $COR^{11}$ or $R^{13}$,
$R^1$ represents $C_1-C_7$-alkyl, $C_3-C_7$-alkenyl or $C_2-C_7$-alkinyl, $R^2$, $R^{11}$ and $R^{13}$ are identical or different and represent $C_1-C_6$-alkyl,
$R^3-R^8$ are identical or different and represent hydrogen or $C_1-C_6$-alkyl,
and wherein
$R^2$ and $R^3$ or $R^3$ and $R^7$, together with the atoms to which they are bonded, can also form a 5- or 6-membered monocyclic ring, and
n represents 1 and
m represents 0.

Compounds of the general formula (I) which are particularly preferably used as repellents are those in which X represents hydrogen or $R^{13}$,
wherein
$R^{13}$ represents $C_1-C_6$-alkyl,
$R^1$ represents $C_1-C_7$-alkyl, $C_3-C_7$-alkenyl or $C_3-C_7$-alkinyl,
$R_4$ to $R_8$ are identical or different and represent hydrogen or $C_1-C_6$-alkyl,
$R^2$ and $R^3$, together with the atoms to which they are bonded, form a 5- or 6-membered monocyclic ring,
n represents 1 and
m represents 0.

Compounds which are furthermore preferred are those in which
$R^1$ represents $C_1-C_7$-alkyl, $C_3-C_7$-alkenyl or $C_3-C_7$-alkinyl,
X represents $COR^{11}$ or $R^{13}$,
$R^2$ and $R^{11}$ are identical or different and represent $C_1-C_6$-alkyl,
$R^3$ to $R^8$ are identical or different and represent hydrogen or $C_1-C_6$-alkyl,
$R^{13}$ represents $C_1-C_6$-alkyl, and
n represents 1 and
m represents 0.

Especially preferred compounds are those of the formula (I) which are used as repellents, wherein m represents 0 and n represents 1,
$R^1$ stands for $C_1-C_4$-alkyl and
$R^2$, $R^{11}$ and $R^{13}$ are identical or different and represent $C_1-C_6$-alkyl,
$R^3$ to $R^8$ represent hydrogen and
X represents hydrogen, $COR^{11}$ or $R^{13}$, wherein $R^{11}$ and $R^{13}$ have the abovementioned meaning.

Compounds of the general formula (I) which are furthermore especially preferably used as repellents are those
in which
m is 0 and
n is 1,
$R^1$ represents $C_3-C_4$-alkyl,
$R^2$ and $R^3$, together with the atoms to which they are bonded, form a 6-membered ring,
$R^4$ to $R^8$ represents hydrogen and
X represents hydrogen and $R^{13}$,
wherein $R^{13}$ represents $C_1-C_4$-alkyl.

The compounds of the general formula (I) are either known or can be prepared by known methods and processes (compare, for example, Cesare Ferri, Reaktionen der organischen Synthese (Reactions of Organic Synthesis), Georg Thieme Verlag Stuttgart, 1978, page 223 and page 450).

The compounds of the formula (I) are accordingly obtained (a) by a process in which the α,ω-aminoalcohols which are known per se or can be prepared by known processes (compare, for example, Cesare Ferri, Reaktionen der org. Synthese (Reactions of Organic Synthesis), Georg Thieme Verlag Stuttgart, 1978, pages 211 et seq. and 496–497), of the formula (II)

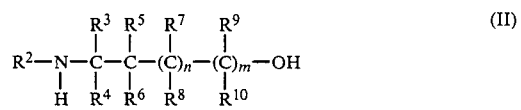

wherein $R^2$ to $R^{10}$, n and m have the meaning given under formula (I), are first reacted with chlorocarbonic acid esters which are known per se, of the formula (III)

wherein $R^1$ has the meaning given under formula (I), if appropriate in the presence of an acid acceptor, such as, for example, triethylamine or potassium carbonate, and if appropriate using a diluent, such as, for example, toluene, $CH_2Cl_2$, tetrahydrofuran or acetonitrile, at temperatures between $-40°$ and $110°$ C.

To prepare compounds of the general formula (I) in which X is other than hydrogen, further acylation/alkylation is then carried out in a second reaction step, if appropriate after isolation of the intermediate product with a free OH group, with carboxylic acid chlorides which are known per se, of the formula (IV)

to prepare compounds of the formula (I) where $X=COR^{11}$; chlorocarbonic acid esters of the formula (V)

to prepare compounds of the formula (I) where $X=COOR^{12}$; or alkyl halides of the formula (VI)

to prepare compounds of the formula (I) where $X=R^{13}$;
wherein, in the formula (IV), (V), (VI),
Y represents chlorine, bromine or iodine, preferably bromine or iodine, and
$R^{11}$ to $R^{13}$ have the abovementioned meaning,
if appropriate in the presence of an acid acceptor, such as, for example, triethylamine or potassium carbonate, or a base, such as sodium hydride or butyllithium, if appropriate using a diluent, such as, for example, toluene, tetrahydrofuran or acetonitrile, at temperatures between $-78°$ and $110°$ C. reacted.

(b) The compounds of the formula (I) are furthermore obtained by a process in which the α,ω-aminoalcohols or α,ω-aminoethers which are known per se or can be prepared by known processes, of the formula (X)

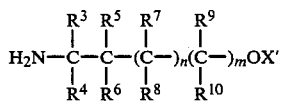

(X)

wherein $R^3$ to $R^{10}$, n, m and $R^{13}$ have the meaning given under formula (I) and wherein X' represents hydrogen or $R^{13}$, are first reacted with chlorocarbonic acid esters which are known per se, of the formula (III), if appropriate in the presence of an acid acceptor, such as, for example, triethylamine or potassium carbonate, and if appropriate using a diluent, such as, for example, toluene, $CH_2Cl_2$, tetrahydrofuran or acetonitrile, at temperatures between $-40°$ C. and $110°$ C.

In a second reaction step, to prepare compounds of the formula (I) in which X does not represent $R^{13}$ or hydrogen, if appropriate after isolation of the intermediate product with the free OH group, further acylation is carried out with carboxylic acid chlorides which are known per se, of the formula (IV), to prepare compounds of the formula (I) where $X=COR^{11}$, or chlorocarbonic acid esters of the formula (V), to prepare compounds of the formula (I) where $X=COOR^{12}$, wherein, in the formulae (IV) and (V), $R^{11}$ and $R^{12}$ have the abovementioned meaning, if appropriate in the presence of an acid acceptor, such as, for example, triethylamine or potassium carbonate, if appropriate using a diluent, such as, for example, toluene, tetrahydrofuran or acetonitrile, at temperatures between $-78°$ and $110°$ C.

In a third reaction step, if appropriate after isolation of the intermediate with a free NH group, further N-alkylation is carried out with alkyl halides of the formula (XI)

$R^2—Y'$           (XI)

to prepare compounds of the formula (I),
wherein
Y' represents chlorine, bromine or iodine, preferably bromine or iodine, and
$R^2$ has the abovementioned meaning,
if appropriate in the presence of a base, such as, for example, sodium hydride or butyllithium, if appropriate using a diluent, such as, for example, toluene or tetrahydrofuran, at temperatures between $-78°$ and $110°$ C.

Working up is carried out by customary methods, for example by extraction of the products with methylene chloride or toluene from the reaction mixture which has been diluted with water, washing the organic phase with water, drying and distillation or so-called "incipient distillation", that is to say by prolonged heating at moderately elevated temperatures under reduced pressure, in order to free the products from the last volatile constituents.

Further purification can be carried out by chromatography on silica gel with, for example, hexane:acetone=7:3 as the mobile phase.

The refractive index, melting point, Rf value or boiling point is used to characterize the compounds.

The present invention also relates to new substituted aminoalcohol derivatives of the formula (VII)

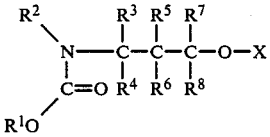

(VII)

in which
X represents hydrogen, $COR^{11}$ or $R^{13}$,
$R^1$ represents optionally substituted alkyl alkenyl or alkinyl radicals,
$R^2$, $R^{11}$ and $R^{13}$ are identical or different and represent optionally substituted alkyl or alkenyl radicals,
$R^3$ to $R^8$ are identical or different and represent hydrogen, or represent optionally substituted alkyl radicals, and wherein $R^2$ and $R^3$ or $R^3$ and $R^7$ or $R^3$ and $R^5$ or $R^5$ and $R^7$, together with the atoms to which they are bonded, can also form an optionally substituted monocyclic ring, with the exception of the following substituent combinations (a) and (b):
(a) X=hydrogen, $R^2$=methyl and $R^1$=tert.-butyl and
(b) X=hydrogen, $R^1$=ethyl, $R^5$=ethyl and $R^6$=ethyl.

The compounds of the formula (VII) are obtained (a) by a process in which the $\alpha,\omega$-aminoalcohols which are known per se or can be prepared by known processes (compare, for example, Cesare Ferri, Reaktionen der org. Synthese (Reactions of Organic Synthesis), Georg Thieme Verlag Stuttgart, 1978, pages 211 et seq. and 496–497), of the formula

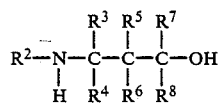

(VIII)

wherein $R^2$ to $R^8$ have the meaning given under formula (VII), are first reacted with carboxylic acid derivatives which are known per se, of the formula (IX)

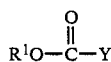

(IX)

wherein
$R^1$ has the meaning given under formula VII and
Y represents halogen or a leaving group customary in amidation reactions, preferably an activating ester radical or a group

if appropriate in the presence of a diluent and if appropriate with the addition of a base.

To prepare compounds of the general formula (VII) in which X is other than hydrogen, further acylation/alkylation is then carried out in a second reaction step, if appropriate after isolation of the intermediate with the free OH group, with carboxylic acid chlorides which are known per se, of the formula (IV)

$R^{11}COCl$     (IV)

to prepare compounds of the formula (VII) where $X=COR^{11}$, or alkyl halides of the formula (VI)

$R^{13}—Y$     (VI)

to prepare compounds of the formula (I) where $X=R^{13}$; wherein, in the formulae (IV) and (VI), Y represents chlorine, bromine or iodine, preferably bromine or iodine, and $R^{11}$ to $R^{13}$ have the abovementioned meaning, if appropriate in the presence of an acid acceptor, such as, for example, triethylamine or potassium carbonate, or a base, such as sodium hydride or butyllithium, if appropriate using a diluent, such as, for example, toluene, tetrahydrofuran or acetonitrile, at temperatures between −78° and 110° C.

(b) The compounds of the formula (VII) are furthermore obtained by a process in which the α,ω-aminoalcohols or α,ω-aminoethers which are known per se or can be prepared by known processes, of the formula (XII)

wherein $R^3$ to $R^8$ have the meaning given under formula (VII) and wherein

X' represents hydrogen or $R^{13}$, wherein $R^{13}$ represents optionally substituted alkyl or alkenyl, are first reacted with chlorocarbonic acid esters which are known per se, of the formula (III), if appropriate in the presence of an acid acceptor, such as, for example, triethylamine or potassium carbonate, and if appropriate using a diluent, such as, for example, toluene, $CH_2Cl_2$, tetrahydrofuran or acetonitrile, preferably at temperatures between −40° C. and 110° C.

In a second reaction step, to prepare compounds of the formula (VII) in which X does not represent $R^{13}$ or hydrogen, if appropriate after isolation of the intermediate with the free OH group, further acylation is carried out with carboxylic acid chlorides which are known per se, of the formula (IV), to prepare compounds of the formula (VII) where $X=COR^{11}$, wherein, in the formulae (IV), $R^{11}$ and $R^{12}$ have the abovementioned meaning, if appropriate in the presence of an acid acceptor, such as, for example, triethylamine or potassium carbonate, if appropriate using a diluent, such as, for example, toluene, tetrahydrofuran or acetonitrile, at temperatures between −78° and 110° C.

In a third reaction, if appropriate after isolation of the intermediate with the free NH group, further N-alkylation is then carried out with alkyl halides of the formula (XI)

to prepare compounds of the formula (VII), wherein

X' represents chlorine, bromine or iodine, preferably bromine or iodine and $R^2$ has the abovementioned meaning, if appropriate in the presence of a base, such as, for example, sodium hydride or butyllithium, if appropriate using a diluent, such as, for example, toluene or tetrahydrofuran, at temperatures between −78° and 110° C.

Working up is carried out by customary methods, for example by extraction of the products with methylene chloride or toluene from the reaction mixture which has been diluted with water, washing the organic phase with water, drying and distillation or so-called "incipient distillation", that is to say by prolonged heating to moderately elevated temperatures under reduced pressure, in order to free the products from the last volatile constituents.

Further purification can be carried out by chromatography on silica gel with, for example, hexane:acetone=7:3 as the mobile phase.

The new substituted α,ω-aminoalcohol derivatives of the general formula (VII) are distinguished by a potent insect- and mite-repelling action. They can also be used in synergistic mixtures with other repellents.

The radicals given in formula (VII) preferably have the following meaning:

The alkyl group in the radicals $R^1$ to $R^{13}$ is straight-chain or branched and contains 1 to 12, preferably 1 to 8 and in particular 1 to 6, carbon atoms. Examples which may be mentioned are methyl, ethyl, n- and i-propyl, n-, i- and t-butyl, n-pentyl and n-hexyl.

Optionally substituted alkenyl is straight-chain or branched alkenyl with preferably 2 to 10, in particular 2 to 7, carbon atoms. Examples which may be mentioned are optionally substituted 2-propenyl, 2-butenyl and 3-butenyl.

Preferred compounds of the general formula (VII) are those in which

X represents hydrogen, $COR^{11}$ or $R^{13}$, $R^1$ represents $C_1$-$C_7$-alkyl, $C_3$-$C_7$-alkenyl or $C_2$-$C_7$-alkinyl, $R^2$, $R^{11}$ and $R^{13}$ are identical or different and represent $C_1$-$C_6$-alkyl, and $R^3$-$R^8$ are identical or different and represent hydrogen or $C_1$-$C_6$-alkyl, and wherein $R^2$ and $R^3$ or $R^3$ and $R^7$, together with the atoms to which they are bonded, can also form a 5- or 6-membered monocyclic ring, with the exception of the following substituent combinations (a) and (b):

(a) X=hydrogen, $R^2$=methyl and $R^1$=tert.-butyl, (b) X=hydrogen, $R^1$=ethyl, $R^5$=ethyl and $R^6$=ethyl.

Particularly preferred compounds of the general formula (VII) are those in which X represents hydrogen or $R^{13}$, wherein $R^{13}$ represents $C_1$-$C_6$-alkyl, $R^1$ represents $C_1$-$C_7$-alkyl or $C_3$-$C_7$-alkenyl, $R_4$ to $R_8$ are identical or different and represent hydrogen or $C_1$-$C_6$-alkyl, and $R^2$ and $R^3$, together with the atoms to which they are bonded, form a 5- or 6-membered monocyclic ring.

Compounds of the formula VII which are furthermore preferred are those in which $R^1$ represents $C_1$-$C_7$-alkyl, $C_3$-$C_7$-alkenyl or $C_2$-$C_7$-alkinyl, X represents hydrogen, $COR^{11}$ or $R^{13}$, $R^2$ and $R^{11}$ are identical or different and represent $C_1$-$C_6$-alkyl, $R^3$ to $R^8$ are identical or different and represent hydrogen or $C_1$-$C_6$-alkyl, and $R^{13}$ represents $C_1$-$C_6$-alkyl, with the exception of the following substituent combinations (a) and (b):

(a) X=hydrogen, $R^2$=methyl and $R^1$=tert.-butyl, (b) X=hydrogen and $R^1$, $R^5$ and $R^6$=ethyl.

Especially preferred compounds of the formula (VII) are those in which $R^1$ represents $C_1$–$C_4$-alkyl, $R^{13}$, $R^2$ and $R^{11}$ are identical or different and represent $C_1$–$C_6$-alkyl, $R^3$ to $R^8$ represent hydrogen and X represents hydrogen, $COR^{11}$ or $R^{13}$, wherein $R^{11}$ and $R^{13}$ have the abovementioned meaning, with the exception of the following substituent combination:

X=hydrogen, $R^2$=methyl and $R^1$=tert.-butyl.

Compounds of the formula (VII) which are furthermore especially preferred are those
in which $R^1$ represents $C_3$–$C_4$-alkyl or $C_3$–$C_4$-alkenyl, $R^2$ and $R^3$, together with the atoms to which they are bonded, form a 6-membered ring, $R^4$ to $R^8$ represent hydrogen and X represents hydrogen or $R^{13}$, wherein $R^{13}$ represents $C_1$–$C_4$-alkyl.

The compounds of the general formula (VII) contain one or more centres of asymmetry and can thus be in the form of diastereomers or diastereomer mixtures.

If, for example, 2-(2-hydroxyethyl)-piperidine and butyl chloroformate are used as starting substances, the reaction of these compounds can be outlined by the following equation:

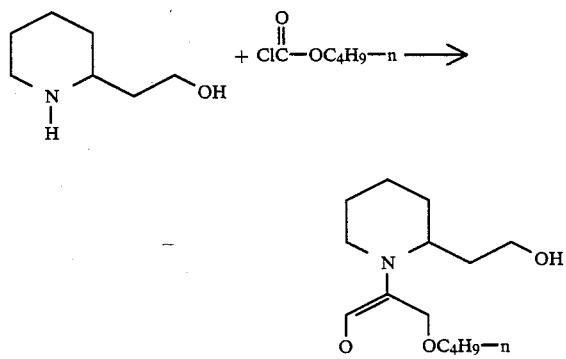

The compounds of the general formula (VIII), (IX), (IV) and (VI) used as starting substances in the preparation of the new compounds of the formula (VII) are generally known compounds of organic chemistry or can be prepared by known processes and methods (compare also the preparation examples).

Possible diluents for the process according to the invention are virtually all the organic diluents which are inert under the process conditions. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, esters, such as methyl and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric acid triamide.

The reaction temperatures can be varied within a substantial range. The reaction is preferably carried out at temperatures between −50° C. and 120° C., preferably between −20° C. and 110° C. The reactions are in general carried out at atmospheric pressure.

The reactions are preferably carried out in the presence of basic auxiliaries. The most favourable amount of base in each case can easily be determined experimentally. Possible bases are preferably those bases which are usually also employed as acid-binding agents. Examples which may be mentioned are: alkyl carbonates and alcoholates, such as sodium carbonate, potassium carbonate, sodium methylate, ethylate and t-butylate and potassium methylate, ethylate and t-butylate, and furthermore aliphatic, aromatic or heterocyclic amines, for example triethylamine, trimethylamine, dimethylaniline, dimethylbenzylamine and pyridine, as well as metal hydrides, such as sodium hydride, or organometallic compounds, such as, for example, n-butyllithium.

For carrying out process (a) according to the invention, 1 to 2 mol, in particular 1 to 1.2 mol, of the compound (IX) are first preferably employed per mol of α,ω-aminoalcohol of the formula (VIII).

In the same way, 1 to 2 mol, preferably 1 to 1.2 mol, of the compounds (IV) or (VI) are employed in the preparation of compounds of the formula (VII) in which X is other than hydrogen, if appropriate after isolation of the intermediate product with the free OH group. If a base is employed, this is used in an amount of 1 to 4 mol, preferably 1 to 1.5 mol, per mol of the intermediate.

For carrying out process (b) according to the invention, 1 to 2 mol, in particular 1 to 1.2 mol, of the compound (III) are first preferably employed per mol of amine of the formula (XII).

In the same way, 1 to 2 mol, preferably 1 to 1.2 mol, of the compound (IV) are employed in the preparation of compounds of the formula (VII) in which X does not represent hydrogen or $R^{13}$, if appropriate after isolation of the intermediate with the free OH group. If a base is employed, this is used in an amount of 1 to 4 mol, preferably 1 to 1.5 mol, per mol of the intermediate.

For the subsequent N-alkylation, 1 to 10 mol, preferably 1 to 1.5 mol, of the compound $R^2$-Y' are employed per mol of the NH-intermediate, if appropriate after prior isolation. If a base is necessary, this is used in an amount of 1 to 4 mol, preferably 1 to 1.5 mol, per mol of the NH-intermediate.

Working up of the compounds of the formula (VII) according to the invention is carried out in a manner analogous to that described above for the preparation of the compounds of the formula (I).

The action of the repellents of the general formula (I or VII) persists for a long time.

They can therefore be used particularly successfully for repelling harmful or troublesome sucking and biting insects and mites.

The sucking insects essentially include the mosquitoes (for example Aedes, Culex and Anopheles species), owl gnats (Phlebotoma), blackfly (Culicoides species), buffalo gnats (Simulium species), biting flies (for example *Stomoxys calcitrans*), tsetse flies (Glossina species), horseflies (Tabanus, Haematopota and Chrysops species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma Lineatum, Dermatobia hominis, Oestrus ovis, Gasterophilus intestinalis* and *Cochliomyia hominovorax*), bugs (for example *Cimex Lectularius, Rhodnius prolixus* and *Triatoma infestans*), lice (for example *Pediculus humanus, Haematopinus suis* and *Damalina ovis*), Louse flies (for example *Melaphagus orinus*), fleas (for example *Pulex irritans, Cthenocephalides canis* and *Xenopsylla cheopis*) and sand fleas (for example *Dermatophilus penetrans*).

The biting insects essentially include cockroaches (for example *Blattella germanica, Periplaneta americana, Blatta orientalis* and *Supella supellectilium*), beetles (for example *Sitophilus granarius, Tenebrio molitor, Dermestes Lardarius, Stegobium paniceum, Anobium punctatum* and *Hylotrupes bajulus*), termites (for example *Reticulitermes lucifugus*) and ants (for example *Lasius niger*).

The mites include ticks (for example *Ornithodorus moubata, Ixodes ricinus, Boophilus microplus* and *Amblyomma hebreum*) and mites in the narrower sense (for example *Sarcoptes scabiei* and *Dermanyssus gallinae*).

The active compounds according to the invention, which can be used undiluted or, preferably, in dilute form, can be converted into the formulations customary for repellents. They can be used in all the presentation forms customary in cosmetics, for example in the form of solutions, emulsions, gels, ointments, pastes, creams, powders, sticks, sprays or aerosols from spray cans.

For use in the non-cosmetic sector, the active compounds can be incorporated, for example, into granules, oily spraying agents or slow release formulations.

The formulations are prepared in a known manner by mixing or diluting the active compounds according to the invention with solvents (for example xylene, chlorobenzenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The active compounds according to the invention can be mixed with one another in the formulations or can also be used as mixtures with other known active compounds (for example sunscreen agents). The formulations in general contain between 0.1 and 95% by weight of active compound, preferably between 0.5 and 90%.

For protection from blood-sucking insects or mites, the active compounds according to the invention are either applied to human or animal skin, or items of clothing and other objects are treated with the active compounds.

The active compounds according to the invention are also suitable as an additive to impregnating agents for, for example, textile webs, articles of clothing and packaging materials, and as an additive to polishing, cleaning and window-cleaning agents.

The following examples for the formulations and the use of the active compounds according to the invention serve to further illustrate the invention.

FORMULATION EXAMPLE 1

A repellent in the form of a lotion for use on the skin is prepared by mixing 30 parts of one of the active compounds according to the invention, 1.5 parts of perfume and 68.5 parts of isopropanol. The isopropanol can be replaced by ethanol.

FORMULATION EXAMPLE 2

A repellent in the form of an aerosol for spraying onto the skin is prepared by formulating 50% of active compound solution, consisting of 30 parts of one of the active compounds according to the invention, 1.5 parts of perfume and 68.5 parts of isopropanol, with 50% of Frigen 11/12 (=halogenated hydrocarbon as a propellent) as a spray can.

FORMULATION EXAMPLE 3

Another spray can is composed of 40% of active compound solution consisting of 20 parts of one of the active compounds according to the invention, 1 part of perfume and 79 parts of isopropanol, and 60% of propane/butane (ratio 15:85).

Individual formulations corresponding to Formulation Examples 1, 2 and 3 have been prepared using the following active compounds: compounds according to Preparation Examples No. 1, 2, 4, 5 and 6.

EXAMPLE A

Repellent test on guinea pigs
Test animal: *Aedes aegypti* (imagines)
Number of test animals: about 5,000
Solvent: ethanol (99.8%)

3 parts by weight of active compound are taken up in 100 parts by volume of solvent.

A guinea pig whose back has been shaved over an area of 50 cm² is fixed in a narrow cage (box) so that only the shaved area is accessible to the mosquitoes. After treatment of the area with 0.4 ml of active compound solution and after the solvent has evaporated, the guineapig, together with its box, is placed in a cage measuring 60×60×60 cm containing test animals of both sexes fed only on sugared water.

The number of mosquitoes which bite the guinea pig is observed for 10 minutes.

The guinea pig is then removed and the test is repeated again after one hour. The test is carried out for a maximum of 9 hours, or until the action stops.

In this test, for example, the following compounds of the preparation examples show a superior action compared with the prior art (diethyltoluamide=Deet):

TABLE A

Repellent test on guinea pigs (*Aedes aegypti*)

| Preparation | | Number of bites after: | |
|---|---|---|---|
| | | $0^h$–$6^h$ | $7^h$–$9^h$ |
| Prep. Ex. No. 1 according to the invention | [piperidine structure with N–C(=O)–O–C$_4$H$_9$(n) and (CH$_2$)$_2$–OH] | 0 | 0.1 |
| Prep. Ex. No. 4 | [piperidine structure with N–C(=O)–O–CH$_2$–CH=CH$_2$ and (CH$_2$)$_2$–OH] | 1.0 | 2.7 |

TABLE A-continued

Repellent test on guinea pigs (*Aedes aegypti*)

| Preparation | Structure | Number of bites after: $0^h$–$6^h$ | $7^h$–$9^h$ |
|---|---|---|---|
| Prep. Ex. No. 5 | piperidine-N-C(=O)-O-C$_3$H$_7$(n), 2-(CH$_2$)$_2$-OH | 1.5 | 3.3 |
| Prep. Ex. No. 6 | piperidine-N-C(=O)-O-CH$_2$-CH(CH$_3$)-CH$_3$, 2-(CH$_2$)$_2$-OH | 0.1 | 1.4 |
| Prep. Ex. No. 2 | piperidine-N-C(=O)-O-C(CH$_3$)$_2$-CH$_3$, 2-(CH$_2$)$_2$-OH | 0 | 6.1 |
| Prep. Ex. No. 36 | CH$_3$-N[(CH$_2$)$_3$-OH]-C(=O)-O-(CH$_2$)-CH(C$_2$H$_5$)-CH$_3$ | 1.2 | 11.8 |
| Prep. Ex. No. 49 | CH$_3$-N[(CH$_2$)$_3$-OH]-C(=O)-O-(CH$_2$)$_2$-CH(CH$_3$)-CH$_3$ | 1.3 | 13.0 |
| Prep. Ex. No. 55 | CH$_3$-N[(CH$_2$)$_3$-O-C(=O)-C$_2$H$_5$]-C(=O)-O-(CH$_2$)$_2$-CH$_3$ | 1.7 | 4.9 |
| Prep. Ex. No. 25 | C$_2$H$_5$-N[(CH$_2$)$_3$-OH]-C(=O)-O-CH$_2$-CH(CH$_3$)-CH$_3$ | 0.4 | 6.0 |
| Prep. Ex. No. 26 | piperidine-N-C(=O)-O-CH(CH$_3$)-C$_2$H$_5$, 2-(CH$_2$)$_2$-OH | 0 | 0.1 |
| Prep. Ex. No. 31 | CH$_3$-N[(CH$_2$)$_3$-OH]-C(=O)-O-CH(CH$_3$)-CH$_2$-CH(CH$_3$)-CH$_3$ | 2.0 | 5.0 |
| Known Deet: | 3-CH$_3$-C$_6$H$_4$-C(=O)-N(C$_2$H$_5$)$_2$ | 2.4 | 14.9 |

Note: "Prep. Ex." means "preparation Example"

EXAMPLE B

Repellent test on guinea pigs
Test animal: *Anopheles albimanus* (Imagines)
Number of test animals: about 1,000
Solvent: ethanol (99.8%)

3 parts by weight of active compound are taken up in 100 parts by volume of solvent.

A guinea pig whose back has been shaved over an area of 50 cm$^2$ is fixed in a narrow cage (box) so that only the shaved area is accessible to the mosquitoes. After treatment of the area with 0.4 ml of active compound solution and after the solvent has evaporated, the guinea pig, together with its box, is placed in a cage measuring 60×60×60 cm containing test animals of both sexes fed only on sugared water.

The number of mosquitoes which bite the guinea pig is observed for 10 minutes.

The guinea pig is then removed and the test is repeated again after one hour. The test is carried out for a maximum of 9 hours, or until the action stops.

In this test, for example, the following compounds of the preparation examples show a superior action compared with the prior art (diethyltoluamide=Deet):

TABLE B

Repellent test on guinea pigs

| Preparation | Structure | Number of bites after: $0^h$–$6^h$ | $7^h$–$9^h$ |
|---|---|---|---|
| Prep. Ex. No. 1 according to the invention | piperidine-N-C(=O)-O-C$_4$H$_9$(n), 2-(CH$_2$)$_2$-OH | 1.1 | 2.4 |
| Prep. Ex. No. 6 | piperidine-N-C(=O)-O-CH$_2$-CH(CH$_3$)-CH$_3$, 2-(CH$_2$)$_2$-OH | 1.5 | 1.4 |

TABLE B-continued

Repellent test on guinea pigs

| Preparation | | Number of bites after: | |
|---|---|---|---|
| | | $0^h$–$6^h$ | $7^h$–$9^h$ |
| Prep. Ex. No. 2 | 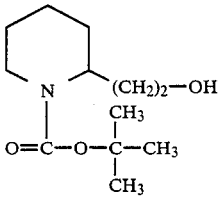 | 0 | 1.5 |
| Prep. Ex. No. 5 | 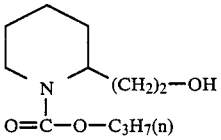 | 0.4 | 7.1 |
| Prep. Ex. No. 4 | 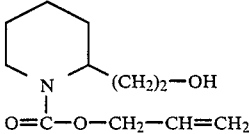 | 0.9 | 6.5 |
| Prep. Ex. No. 48 | 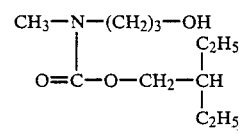 | 0 | 0 |
| Prep. Ex. No. 49 | 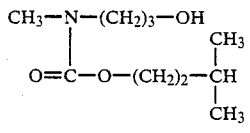 | 0.1 | 4.0 |
| Prep. Ex. No. 25 | 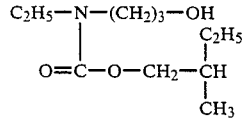 | 0.3 | 2.0 |
| Prep. Ex. No. 26 | 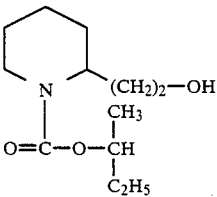 | 0.1 | 0.2 |
| Prep. Ex. No. 36 | 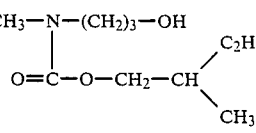 | 0 | 0.2 |
| known Deet: | 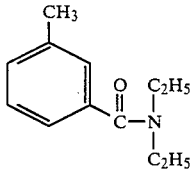 | 1.0 | 5.0 |

PREPARATION EXAMPLES

Example 1

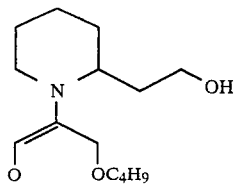

1-(Butoxycarbonyl)-2-(2-hydroxyethyl)-piperidine 6.5 g (0.05 mol) of 2-(2-hydroxyethyl)-piperidine and 10 ml of triethylamine are dissolved in 300 ml of tetrahydrofuran, and 7.5 g (0.55 mol) of butyl chloroformate are added at −20° C.

The mixture is stirred at 20° C. for 24 hours and then extracted with methylene chloride/water. After the organic phase has been dried using magnesium sulphate, the solvent is distilled off in vacuo and the residue is then distilled in a bulb tube oven.

Yield: 5.6 g (=49% of theory).
Boiling point (bulb tube): 120°–130° C./0.25 mbar.

EXAMPLE 2

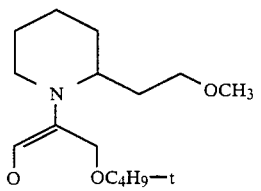

1-(t-Butoxycarbonyl)-2-(2-methoxyethyl)-piperidine 1.1 ml of a % strength butyllithium solution in hexane are added to 0.5 g of 1-(t-butoxycarbonyl)-2-(2-hydroxyethyl)-piperidine (0.002 mol) in 50 ml of tetrahydrofuran at −78° C.

The mixture is heated at 20° C. for 1 hour and at 40° C. for 4 hours and cooled to 20° C., and 5 ml of methyl iodide (0.08 mol) are added to the reaction mixture. The mixture is heated at 40° C. for a further 24 hours and is then poured onto 300 ml of ice-water. It is then extracted several times with methylene chloride. After the organic phase has been dried using magnesium sulphate and the solvent has been distilled off, the residue is chromatographed on about 200 g of silica gel (mobile phase: hexane: ethyl acetate=7:3). After the solvent has been distilled off, 0.3 g (=62% of theory) of 1-(butoxycarbonyl)-2-(2-methoxyethyl)-piperidine is obtained with a refractive index $n_D^{20}$ of 1.4613.

EXAMPLE 3

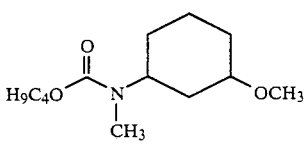

26 g (0.2 mol) of 1-amino-3-methoxycyclohexane and 35 ml of triethylamine (0.25 mol) are dissolved in 500 ml of tetrahydrofuran, and 30 ml (0.24 mol) of butyl chloroformate are added at 20° C. The mixture is stirred at 20° C. for 1 day, the solid is filtered off, the solvent is distilled off, the residue is taken up in methylene chloride and the mixture is filtered over silica gel. Renewed distillation of the solvent gives 36 g (78% of theory) of 1-(N-butoxycarbonyl-)amino-3-methoxycyclohexane.

For further reaction, 11.5 g (0.05 mol) of this compound are dissolved in 150 ml of tetrahydrofuran, and 2.2 g (0.073 mol) of sodium hydride (80% strength in paraffin) are added at 20° C. The mixture is heated under reflux for 4 hours and 10 ml (0.16 mol) of methyl iodide are then added to the reaction mixture at 20° C. The mixture is heated under reflux for 1 hour, 50 ml of ammonium chloride solution are first added, followed by methylene chloride/water, the organic phase is dried using magnesium sulphate and the solvent is distilled off. The residue is then filtered over silica gel with hexane: acetone=1:1. 8.4 g (69% of theory) of 1-(N-butoxycarbonyl-N-methyl)-3-methoxycyclohexane with a refractive index $n_D^{20}$ of 1.4632 are obtained.

The following compounds are obtained analogously:

General formula (VII)

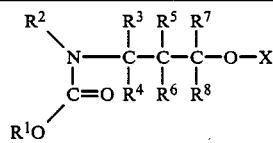

| Preparation Ex. No. | $R^1$ | $R^2$ | $R^3$ | $R^4$ | $R^5$ | $R^6$ | $R^7$ | $R^8$ | X | Physical data ($n_D^{20}$) |
|---|---|---|---|---|---|---|---|---|---|---|
| 4 | $CH_2=CH-CH_2-$ | $-CH_2-CH_2-CH_2-CH_2$ | | H | H | H | H | H | H | 1.4893 |
| 5 | $n-C_3H_7$ | " | | " | " | " | " | " | " | 1.4761 |
| 6 | $(CH_3)_2CH-CH_2-$ | " | | " | " | " | " | " | " | 1.4710 |
| 7 | $n-C_4H_9-$ | $CH_3$ | H | " | " | " | " | " | " | 1.4705 |
| 8 | $(C_2H_5)CH(CH_3CH_2$ | $-CH_2-CH_2-CH_2-CH_2-$ | | " | " | " | " | " | " | |
| 9 | $t-C_4H_9$ | $-CH_2-CH_2-CH_2-CH_2-$ | | " | " | " | " | " | " | 1.4705 |
| 10 | $n-C_4H_9$ | $n-C_4H_9$ | H | " | " | " | " | " | " | 1.4506 |
| 11 | $n-C_4H_9$ | $CH_3$ | H | " | " | " | " | " | $COCH_3$ | 1.4423 |
| 12 | $n-C_4H_9$ | $t-C_4H_9$ | H | H | H | H | H | H | H | |
| 13 | " | " | " | " | " | " | " | " | $COCH_3$ | |
| 14 | " | $n-C_4H_9$ | " | " | " | " | " | " | $COCH_3$ | 1.4436 |
| 15 | $C_2H_5$ | $t-C_4H_9$ | " | " | " | " | " | " | $COCH_3$ | |
| 16 | $(CH_3)_2CHCH_2$ | $t-C_4H_9$ | " | " | " | " | " | " | H | |
| 17 | $(CH_3)_3CCH_2$ | $-CH_2-CH_2-CH_2-CH_2-$ | | " | " | " | " | " | " | |
| 18 | $(CH_3)_2CHCH_2CH_2$ | " | | " | " | " | " | " | " | |
| 19 | $C_2H_5$ | $t-C_4H_9$ | H | " | " | " | " | " | " | |
| 20 | $(C_2H_5)CHCH_2$ | $-CH_2-CH_2-CH_2-CH_2-$ | | " | " | " | " | " | " | |
| 21 | $n-C_4H_9$ | $CH_3$ | H | " | " | " | " | " | $CH_3$ | |
| 22 | $t-C_4H_9$ | $CH_3$ | H | H | H | H | H | H | H | 1.4415 (Kp$_{0.08}$ 120° C.) |
| 23 | $t-C_4H_9$ | $CH_3$ | H | H | H | H | H | H | $COCH_3$ | 1.4261 (Kp$_{0.05}$ 110° C.) |
| 24 | $n-C_4H_9$ | $(CH_3)_3C-CH_3$ | H | H | H | H | H | H | $COCH_3$ | 1.4534 |
| 25 | $(C_2H_5)CH(CH_3)CH_2$ | $C_2H_5$ | H | H | H | H | H | H | H | 1.4490 |
| 26 | $(C_2H_5)(CH_3)CH$ | $-(CH_2)_4-$ | | H | H | H | H | H | H | 1.4717 |
| 27 | $(n-C_3H_7)(CH_3)CH$ | $-(CH_2)_4-$ | | H | H | H | H | H | H | 1.4097 |
| 28 | $CH_3OCH_2CH_2$ | $CH_3$ | H | H | H | H | H | H | H | 1.4544 |
| 29 | $(n-C_3H_7)(CH_3)CH$ | $CH_3$ | H | H | H | H | H | H | H | 1.4458 |
| 30 | $(C_2H_5)(CH_3)CH$ | $CH_3$ | H | H | H | H | H | H | H | 1.4452 |
| 31 | $(i-C_3H_7)CH_2(CH_3)CH$ | $CH_3$ | H | H | H | H | H | H | H | 1.4457 |
| 32 | $(i-C_3H_7)CH_2(CH_3)CH$ | $-(CH_2)_4-$ | | H | H | H | H | H | H | 1.7064 |
| 33 | $(n-C_3H_7)(CH_3)CH$ | $CH_3$ | H | H | H | H | H | H | $COCH_3$ | 1.4450 |
| 34 | $(C_2H_5)(CH_3)CH$ | $CH_3$ | H | H | H | H | H | H | $COCH_3$ | 1.4443 |
| 35 | $(i-C_3H_7)CH_2(CH_3)CH$ | $CH_3$ | H | H | H | H | H | H | $COCH_3$ | 1.4455 |
| 36 | $(C_2H_5)CH(CH_3)CH_2$ | $CH_3$ | H | H | H | H | H | H | H | 1.4715 |
| 37 | $(C_2H_5)CH(CH_3)CH_2$ | $C_2H_5$ | H | H | H | H | H | H | H | 1.4490 |
| 38 | $(C_2H_5)CH(CH_3)CH_2$ | $n-C_3H_7$ | H | H | H | H | H | H | H | |
| 39 | $(C_2H_5)CH(CH_3$ | $-(CH_2)_2CH(CH_3)CH_2-$ | | H | H | H | H | | H | |
| 40 | $n-C_4H_9$ | $-(CH_2)_2CH(CH_3)CH_2-$ | | H | H | H | H | | H | |
| 41 | $(C_2H_5)CH(CH_3)$ | $-CH_2-CH(C_2H_5)CH_2CH_2-$ | | H | H | H | H | | H | |
| 42 | $n-C_4H_9$ | $-CH_2-CH(C_2H_5)CH_2CH_2-$ | | H | H | H | H | | H | |
| 43 | $(C_2H_5)CH(CH_3)CH_2$ | $CH_3$ | $CH_3$ | H | H | H | H | H | H | |
| 44 | $(C_2H_5)CH(CH_3)CH_2$ | $C_2H_5$ | $CH_3$ | H | H | H | H | H | H | |
| 45 | $CH_3$ | $n-C_4H_9$ | H | H | H | H | H | H | H | |
| 46 | $CH_3$ | $CH_3-CH=CH-CH_2$ | H | H | H | H | H | H | H | |
| 47 | $CH_3$ | $CH_2=CH-CH_2$ | H | H | H | H | H | H | H | |
| 48 | $(C_2H_5)_2CHCH_2$ | $CH_3$ | H | H | H | H | H | H | H | 1.4533 |
| 49 | $(CH_3)_2CHCH_2CH_2$ | $CH_3$ | H | H | H | H | H | H | H | 1.4508 |
| 50 | $(CH_3)_3CCH_2$ | $CH_3$ | H | H | H | H | H | H | H | 1.4471 |

-continued

General formula (VII)

$$\begin{array}{c} R^2 \\ \phantom{R^2}\diagdown \\ \phantom{R^2}N\text{---}C\text{---}C\text{---}C\text{---}O\text{---}X \\ \phantom{R^2}\diagup \phantom{N}| \phantom{---}| \phantom{-}| \phantom{-}| \\ \phantom{R^2}C=O\; R^4\; R^6\; R^8 \\ \phantom{R^2}\diagup \\ R^1O \end{array}$$
with $R^3$, $R^5$, $R^7$ on upper carbons.

| Preparation Ex. No. | R$^1$ | R$^2$ | R$^3$ | R$^4$ | R$^5$ | R$^6$ | R$^7$ | R$^8$ | X | Physical data ($n_D^{20}$) |
|---|---|---|---|---|---|---|---|---|---|---|
| 51 | (C$_2$H$_5$)$_2$CHCH$_2$ | CH$_3$ | H | H | H | H | H | H | COCH$_3$ | 1.4469 |
| 52 | (C$_2$H$_5$)(CH$_3$)CHCH$_2$ | CH$_3$ | H | H | H | H | H | H | COCH$_3$ | 1.4450 |
| 53 | (CH$_3$)$_2$CHCH$_2$CH$_2$ | CH$_3$ | H | H | H | H | H | H | COCH$_3$ | 1.4426 |
| 54 | (CH$_3$)$_3$CCH$_2$ | CH$_3$ | H | H | H | H | H | H | COCH$_3$ | 1.4406 |
| 55 | CH$_3$—(CH$_2$)$_2$—CH$_2$ | CH$_3$ | H | H | H | H | H | H | COC$_2$H$_5$ |  |
| 56 | CH$_2$=CH—CH$_2$CH$_2$ | —(CH$_2$)$_4$— |  | H | H | H | H | H | H | 1.4920 |
| 57 | CH$_3$—CH=CH—CH$_2$— | —(CH$_2$)$_4$— |  | H | H | H | H | H | H | 1.4920 |
| 58 | CH$_2$=CH—CH$_2$CH$_2$— | CH$_3$ | H | H | H | H | H | H | H | 1.4625 |
| 59 | CH$_3$—CH=CH—CH$_2$— | CH$_3$ | H | H | H | H | H | H | H | 1.4690 |
| 60 | CH$_3$—CH=CH—CH$_2$— | CH$_3$ | H | H | H | H | H | H | COCH$_3$ | 1.4576 |
| 61 | CH$_2$=CH—CH$_2$—CH$_2$— | CH$_3$ | H | H | H | H | H | H | COCH$_3$ | 1.4522 |
| 62 | CH$_3$—C≡C—CH$_2$— | —(CH$_2$)$_4$— |  | H | H | H | H | H | H | 1.4986 |
| 63 |  | —(CH$_2$)$_4$— |  | H | H | H | H | H | H | 1.4835 |

PREPARATION OF COMPOUNDS OF THE GENERAL FORMULA (VIII)

N-Butylamino-propanol-1,3

48 g (0.5 mol) of 1,3-dichloropropanol are added to 500 ml of butylamine and 1 g of potassium iodide and the mixture is heated under reflux for 2 days. It is then extracted with methylene chloride/water, the organic phase is dried using magnesium sulphate and concentrated on a rotary evaporator, and the residue is distilled. 52 g (=79% of theory) of N-butylamino-propanol-1,3 with a boiling point: bp. 125° C./30 mbar are obtained.

We claim:

1. A substituted α,ω-aminoalcohol derivative of the formula

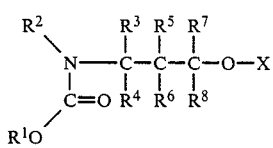

in which

X represents hydrogen, COR$^{11}$ or R$^{13}$,

R$^1$ represents an optionally substituted alkyl, alkenyl or alkinyl radical said substituents being cycloalkyl, C$_1$-C$_4$-alkoxy, halogen and CN, R$^{11}$ and R$^{13}$ are identical or different and represent optionally substituted alkyl or alkenyl radicals, R$^4$ to R$^8$ are identical or different and represent hydrogen, or represent optionally substituted alkyl radicals, and wherein R$^2$ and R$^3$ together with the atoms to which they are bonded form an optionally substituted 5 to 7-membered saturated monocyclic ring, with the exception of the following substituent combinations (a) and (b):

(a) X=hydrogen, R$^1$=ethyl, R$^5$=ethyl and R$^6$=ethyl and (b) R$^2$ and R$^3$ together with the atoms to which they are bonded form a 5-membered ring, R$^1$ is t-butyl and R$^4$, R$^5$, R$^6$, R$^7$, R$^8$ and X are H.

2. A substituted α,ω-aminoalcohol derivative according to claim 1, in which

X represents hydrogen, COR$^{11}$ or R$^{13}$,

R$^1$ represents C$_1$-C$_7$-alkyl, C$_3$-C$_7$-alkenyl or C$_2$-C$_7$-alkinyl,

R$^{11}$ and R$^{13}$ are identical or different and represent C$_1$-C$_6$-alkyl, and R$^4$-R$^8$ are identical or different and represent hydrogen or C$_1$-C$_6$-alkyl, and wherein R$^2$ and R$^3$, together with the atoms to which they are bonded, form a 5- or 6-membered saturated monocyclic ring.

3. A substituted α,ω-aminoalcohol derivative according to claim 1, in which

R$^{13}$ represents C$_1$-C$_6$-alkyl,

R$^1$ represents C$_1$-C$_7$-alkyl or C$_3$-C$_7$-alkenyl,

R$_4$ to R$_8$ are identical or different and represent hydrogen or C$_1$-C$_6$-alkyl, and R$^2$ and R$^3$, together with the atoms to which they are bonded, form a 5- or 6-membered saturated monocyclic ring.

4. A substituted α,ω-amino-alcohol derivative according to claim 1, wherein

R$^1$ is (C$_2$H$_5$)(CH$_3$)CH,

R$^2$ and R$^3$ taken together is —(CH$_2$)$_4$—

R$_4$, R$_5$, R$_6$, R$_7$, R$_8$ and X are each hydrogen and having the formula

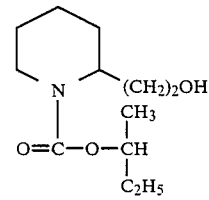

* * * * *